(12) United States Patent
Alam et al.

(10) Patent No.: US 9,896,772 B2
(45) Date of Patent: Feb. 20, 2018

(54) MODULAR CHEMIRESISTIVE SENSOR

(71) Applicant: InnoSense, LLC, Torrance, CA (US)

(72) Inventors: Maksudul M. Alam, Glendora, CA (US); Uma Sampathkumaran, Torrance, CA (US)

(73) Assignee: INNOSENSE LLC, Torrance, CA (US)

( * ) Notice: Subject to any disclaimer, the term of this patent is extended or adjusted under 35 U.S.C. 154(b) by 83 days.

(21) Appl. No.: 14/658,034

(22) Filed: Mar. 13, 2015

(65) Prior Publication Data
US 2015/0260668 A1 Sep. 17, 2015

Related U.S. Application Data

(60) Provisional application No. 61/952,557, filed on Mar. 13, 2014.

(51) Int. Cl.
| | | |
|---|---|---|
| C25B 3/00 | (2006.01) |
| G01N 27/414 | (2006.01) |
| G01N 27/327 | (2006.01) |
| B82Y 30/00 | (2011.01) |

(52) U.S. Cl.
CPC ........... *C25B 3/00* (2013.01); *G01N 27/3278* (2013.01); *G01N 27/414* (2013.01); *G01N 27/4145* (2013.01); *B82Y 30/00* (2013.01)

(58) Field of Classification Search
CPC .... C25B 3/00; G01N 27/3278; G01N 27/414; G01N 27/4145; B82Y 30/00
See application file for complete search history.

(56) References Cited

U.S. PATENT DOCUMENTS

| | | |
|---|---|---|
| 5,222,388 A | 6/1993 | Sinha et al. |
| 5,536,473 A | 7/1996 | Monkman et al. |
| 5,869,007 A | 2/1999 | Jang et al. |
| 7,226,530 B2 | 6/2007 | Weiller et al. |
| 7,291,503 B2 | 11/2007 | Swager |
| 7,939,024 B2 | 5/2011 | Brongersma et al. |
| 7,948,041 B2 | 5/2011 | Bryant et al. |

(Continued)

OTHER PUBLICATIONS

Zheng et al. Multiplexed electrical detection of cancer markers with nanowire sensor arrays, Oct. 2005, Nature Biotechnology, vol. 23, No. 10.*

*Primary Examiner* — Melanie Yu Brown
(74) *Attorney, Agent, or Firm* — Koppel, Patrick, Heybl & Philpott

(57) ABSTRACT

The present invention relates to a modular chemiresistive sensor. In particular, a modular chemiresistive sensor for hypergolic fuel and oxidizer leak detection, carbon dioxide monitoring and detection of disease biomarkers. The sensor preferably has two gold or platinum electrodes mounted on a silicon substrate where the electrodes are connected to a power source and are separated by a gap of 0.5 to 4.0 μM. A polymer nanowire or carbon nanotube spans the gap between the electrodes and connects the electrodes electrically. The electrodes are further connected to a circuit board having a processor and data storage, where the processor can measure current and voltage values between the electrodes and compare the current and voltage values with current and voltage values stored in the data storage and assigned to particular concentrations of a pre-determined substance such as those listed above or a variety of other substances.

21 Claims, 16 Drawing Sheets

(56) References Cited

U.S. PATENT DOCUMENTS

| | | |
|---|---|---|
| 7,956,427 B2 | 6/2011 | Lieber et al. |
| 8,012,326 B2 | 9/2011 | Weiller et al. |
| 8,030,100 B2 | 10/2011 | Besnard et al. |
| 8,138,005 B2 | 3/2012 | Jang et al. |
| 8,152,991 B2 | 4/2012 | Briman et al. |
| 8,178,355 B2 | 5/2012 | Acharya et al. |
| 8,187,865 B2 | 5/2012 | Yun et al. |
| 8,338,097 B2 | 12/2012 | Castro et al. |
| 8,394,330 B1 | 3/2013 | Lewis et al. |
| 8,525,237 B1 | 9/2013 | Weiss et al. |
| 8,668,874 B2 | 3/2014 | Tao et al. |
| 8,673,216 B2 | 3/2014 | Chen et al. |
| 8,683,672 B2 | 4/2014 | Deshusses et al. |
| 8,703,500 B2 | 4/2014 | Zang et al. |
| 8,951,473 B2 | 2/2015 | Wang et al. |
| 8,961,880 B2 | 2/2015 | Virji et al. |
| 2004/0241164 A1* | 12/2004 | Bales .............. C07K 16/18 424/145.1 |
| 2004/0241436 A1* | 12/2004 | Hsieh .............. D01D 5/0007 428/361 |
| 2005/0036905 A1* | 2/2005 | Gokturk ............ B82Y 15/00 422/400 |
| 2005/0072213 A1 | 4/2005 | Besnard et al. |
| 2005/0129573 A1 | 6/2005 | Gabriel et al. |
| 2007/0114138 A1 | 5/2007 | Krasteva et al. |
| 2007/0269900 A1 | 11/2007 | Lebret et al. |
| 2007/0281362 A1 | 12/2007 | Vink et al. |
| 2009/0275143 A1 | 11/2009 | Misra et al. |
| 2009/0294303 A1 | 12/2009 | Fischer et al. |
| 2010/0000883 A1 | 1/2010 | Morrin et al. |
| 2010/0005858 A1 | 1/2010 | Virji et al. |
| 2010/0089772 A1* | 4/2010 | Deshusses .......... G01N 27/127 205/781 |
| 2010/0273665 A1 | 10/2010 | Haick et al. |
| 2010/0282245 A1 | 11/2010 | Star et al. |
| 2010/0325073 A1 | 12/2010 | Haick |
| 2011/0287551 A1 | 11/2011 | Weiller et al. |
| 2011/0300637 A1 | 12/2011 | Virji et al. |
| 2012/0097917 A1 | 4/2012 | Zhou et al. |
| 2012/0134880 A1* | 5/2012 | Kurkina ........... G01N 21/6489 422/82.01 |
| 2012/0298530 A1 | 11/2012 | Yunus et al. |
| 2013/0034910 A1 | 2/2013 | Haick et al. |
| 2013/0040397 A1 | 2/2013 | Star et al. |
| 2013/0115705 A1 | 5/2013 | Patolsky et al. |
| 2013/0209991 A1* | 8/2013 | Wang ............... A61B 5/1473 435/5 |
| 2014/0021067 A1 | 1/2014 | Samuilov et al. |
| 2014/0154785 A1 | 6/2014 | Yun et al. |
| 2015/0008486 A1 | 1/2015 | Bryant et al. |
| 2015/0056471 A1* | 2/2015 | Joo ................. D01D 5/0015 428/687 |

* cited by examiner

MODULAR CHEMIRESISTIVE SENSOR

This application claims priority based on U.S. Pat. Ser. No. 61/952,557 filed Mar. 13, 2014, which is incorporated herein in its entirety.

This invention was made with government support under (1) Grant: DE-SC0008210—awarded by Department of Energy, Chicago, Ill., (2) Grant: 5R43AG029006, awarded by National Institutes of Health, Washington, D.C., and (3) Contract: HQ0147-13-C-7333—awarded by Missile Defense Agency (MDA), Redstone Arsenal, Ala.

FIELD

The present invention relates to a modular chemiresistive sensor. In particular, a modular chemiresistive sensor for hypergolic fuel and oxidizer leak detection, carbon dioxide monitoring and detection of disease biomarkers.

BACKGROUND

Missile systems, such as the Theatre High Altitude Area Defense (THAAD) ballistic missiles, use hypergolic fuels and oxidizers as a means of propulsion. These hypergolic propellants and oxidizers are corrosive, carcinogenic, toxic, and present fire hazards when a leak is present. Their storage and deployment is thus crucial to ensure personnel safety and mission success. The hypergolic fuel used in missiles is hydrazine or monomethyl hydrazine (MMH), and the oxidizer used in missiles is mixed oxides of nitrogen (MON-25) that is a mixture of dinitrogen tetroxide ($N_2O_4$), nitrogen dioxide ($NO_2$) and nitric oxide (NO). $N_2O_4$ is a dimer of $NO_2$. Under equilibrium conditions, nitrogen tetroxide (NTO) exists as a mixture of $N_2O_4$ and $NO_2$. Therefore, detection of MMH as a hypergolic fuel and $NO_2$ as an oxidizer would indicate a leak in the system.

Electrochemical, chemiluminescence, chemical resistance, absorption, and fluorescence-based detection systems have been developed for the detection of hypergolic fuel and oxidizer leaks. However, these leak detecting sensor devices suffer from drawbacks such as lack of specificity, less effective operation at elevated temperatures, and cell leakage problems leading to maintenance challenges. In addition, the prior art electrochemical monitoring devices can operate in the range −20° C. to +71° C. However, the response time of prior art electrochemical systems at −20° C. is typically 55 minutes at 100 ppm for $NO_2$, and their sensitivity is typically about 100 ppm for both MMH and $NO_2$. Prior art systems also should be replaced annually—which is a maintenance burden and drives system lifecycle costs. Thus, the development of a highly reliable and accurate transducer element to detect rapid changes in concentration of hypergolic fuels and oxidizers within a tactical leak detection subsystem is desired.

Atmospheric levels of carbon dioxide ($CO_2$) have risen significantly from pre-industrial levels of 280 ppm to present levels of 384 ppm. Predictions on future energy use indicate a continued increase of atmospheric $CO_2$ unless major changes are made in the way energy is produced and how carbon is managed. Due to current concerns about global climate change related to increased $CO_2$ emissions, efforts are underway to better utilize both terrestrial and geologic $CO_2$ sinks as forms of carbon management, offsetting emissions from fossil fuel combustion and other human activities. The storage of industrially generated $CO_2$ in deep geologic formations is considered a viable method and important for reducing $CO_2$ (green house emissions) from the atmosphere. Roughly a billion metric tons of $CO_2$ has to be sequestered annually to make an impact. The Department of Energy (DOE) carbon sequestration "Monitoring Verification and Accounting (MVA)" program requires sensors to monitor, measure and account for 99% of $CO_2$ in the injection zones to confirm safe and permanent storage of $CO_2$ in geologic formations, especially in the near-surface and subsurface environments over a large area with improved accuracy and long-term durability. Reliable and cost-effective monitoring systems are critical to safe permanent storage. Light Detection and Ranging (LIDAR) or satellite-based technologies are only effective for atmospheric or above ground $CO_2$ monitoring. By the time leaked $CO_2$ appears above the surface, significant damage may have occurred to ground water and the surrounding ecosystem. Therefore, a reliable and cost-effective near-surface/subsurface $CO_2$ monitoring system is critical to confirming the safe and permanent storage of 99% of $CO_2$ in the geologic injection zones.

Alzheimer's disease (AD) is the most common form of dementia. AD and other forms of dementia impose a tremendous financial burden on the health care system and the general economy. According to the Alzheimer's Association, the cost of caring for AD patients is estimated to be $203 billion in the United States in 2013. In addition, 15.4 million Americans provide unpaid care valued at $216 billion for persons with AD and other dementias. Unless addressed, the cost of AD is estimated to reach $1.2 trillion by 2050. Therapeutics can delay the onset of AD to an extent; however their efficacy depends on early diagnosis. In 2012, the U.S. Food and Drug Administration (FDA) approved Amyvid, a radiopharmaceutical imaging agent for positron emission tomography (PET) scans that measure the brain β-amyloid plaque density in-vivo in patients. The PET scans are highly sensitive. However, Amyvid PET scan is not a test for predicting the development of AD-associated dementia and is not intended to monitor patient responses to AD therapy. Amyvid does not replace other diagnostic tests used in the evaluation of cognitive impairment. In addition, PET scans are costly, time consuming, require skilled personnel, and cannot be used as a point-of-care application in doctor's offices and clinics. Another diagnostic method based on a flow cytometric test of Aβ phagocytosis for the detection of AD biomarkers in blood was reported. Neither of these approaches can easily be converted into a cost-effective diagnostic or research tool. Despite the utmost importance, no cost-effective biosensor technologies have been marketed to detect AD biomarkers. Therefore, there is an urgent need to develop technologies for AD screening and early presymptomatic diagnosis. Developing a simple and low-cost biosensor for reliable early diagnosis of AD in point of care facilities is needed.

Cancer is a group of diseases characterized by uncontrolled growth and spread of abnormal cells. It is the leading cause of death worldwide. The United States National Cancer Institute Society has estimated that there are 1,444, 920 new cases of cancer and about 559,650 deaths in the United States each year—more than 1500 deaths per day. The National Institutes of Health estimates that the overall costs for cancer in each year are $206.3 billion: $78.2 billion for direct medical costs; $17.9 billion for indirect morbidity costs; and $110.2 billion for indirect mortality costs. This problem underscores the need for reliable and cost-effective methods for early detection and diagnosis of cancer. A device to monitor cancer therapy progress is also needed. There are several different kinds of cancer. For example: (i) Prostate cancer (PC) is the most common type of cancer found in American men. The American National Cancer Society estimates that there are 218,890 new cases of PC and 27,050 deaths in the United States in each year. PC is the second leading cause of cancer death in men in the United States. Prostate specific antigen (PSA) is the over-expressed biomarker of PC, and is crucial for the detection and diagnosis of PC. (ii) Breast cancer (BC) is the most frequently diagnosed cancer in women. The American National Cancer Society estimates that there will be about 240,510 new cases of breast cancer among women and, as estimated, 40,910 breast cancer deaths (40,460 women and 450 men) are expected in the United States each year. BC ranks second among cancer deaths in women. A protein called human epidermal growth factor receptor 2 (HER-2/neu) is overexpressed in about 20-30% of BCs, which tend to be more aggressive. This overexpressed HER-2/neu protein is an important therapeutic target/biomarker for diagnosis and prognosis of BC. (iii) Lung cancer (LC) accounts for the most cancer related deaths in both men and women. An estimated 213,380 new cases and 160,390 deaths, accounting for about 29% of all cancer deaths, are expected to occur in the United States in each year. Epithelial cell adhesion molecule (EpCAM) protein is an important biomarker of LC. A primary cause of poor survival rates is that many cancers are detected late, after they have spread or metastasized to distant sites. For most types of cancer, the earlier the detection the greater the chances of survival. Therefore, there is an urgent need for devices or methods that can accurately and reproducibly measure multiple cancer biomarkers or circulating tumor cells in bodily fluids or other specimens obtained by minimally invasive methods.

SUMMARY OF THE INVENTION

The present invention relates to a modular chemiresistive sensor. In particular, a modular chemiresistive sensor for hypergolic fuel and oxidizer leak detection, carbon dioxide monitoring and detection of disease biomarkers. The sensor preferably has two gold or platinum electrodes mounted on a silicon substrate where the electrodes are connected to a power source and are separated by a gap of 0.5 to 4.0 µM. A polymer nanowire or carbon nanotube spans the gap between the electrodes and connects the electrodes electrically. The electrodes are further connected to a circuit board having a processor and data storage, where the processor can measure current and voltage values between the electrodes and compare the current and voltage values with current and voltage values stored in the data storage and assigned to particular concentrations of a pre-determined substance such as those listed above or a variety of other substances.

BRIEF DESCRIPTION OF THE DRAWINGS

The present invention described herein will become apparent from the following detailed description considered in connection with the accompanying drawings, which disclose several embodiments of the invention. It should be understood, however, that the drawings are designed for the purpose of illustration and not as limits of the invention.

DETAILED DESCRIPTION OF PREFERRED EMBODIMENTS

Figure 1:
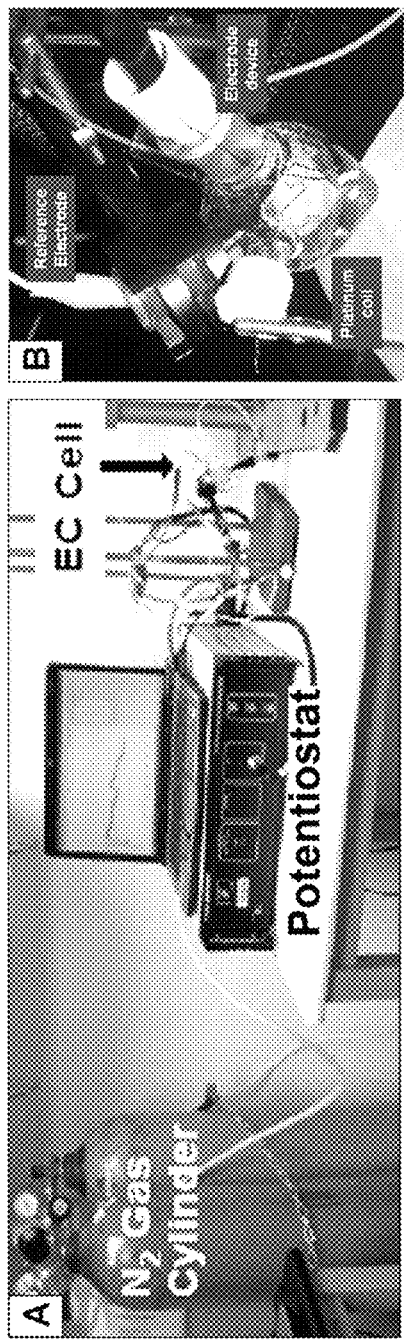
FIG. 1 is a photograph of (A) a preferred lab set up to perform electro-polymerization and (B) a small volume electrochemical cell with electrodes dipped in monomer solution.

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident however, that such embodiment(s) may be practiced without these specific details.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

In this disclosure, a reliable polymer nanowire or carbon nanotube microelectronic hypergolic leak detector (PNMD) using an innovative sensing technology for sensitive and accurate detection of MMH and $NO_2$ under dry nitrogen is described. The term PNMD will be used throughout this application generally to refer to the preferred embodiment of a sensor, though not always for detection of hypergolic leaks. As will be shown, the sensors can be configured to detect other substances.

Figure 4:
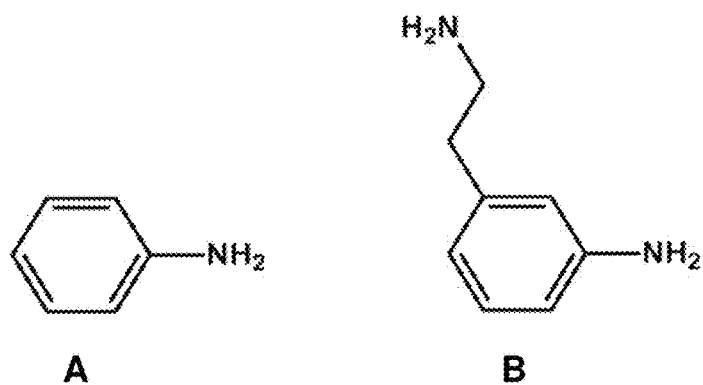
FIG. 4 is diagram of electroactive monomers (A) aniline and (B) amine functionalized 2-(2-aminoethyl) aniline for generating conducting polymer nanowires for sensing MMH and $NO_2$.

Miniaturized and low-power consuming PNMDs are fabricated by direct and site-specific growth of polymer nanowires (or carbon nanotubes) at patterned microchannel electrode junctions. The nanowires are preferably grown from electroactive aniline and functionalized aniline monomers (FIG. 4) using a template-free electrochemical method.

Referring now to FIG. 1, a preferred lab set up for direct electrochemical growth of polymer nanowires in a gap between two electrodes is shown. Preferably, an aqueous solution of an electroactive monomer in 1.0M nitric acid, perchloric acid or hydrochloric acid is used to generate the conducting polymer nanowires. A concentration of a monomer is preferably varied from 0.1M to 0.5M to generate different densities of nanowires. A small volume flask is filled with approximately 16 ml of monomer solution in which a wire-bonded electrode junction device is submerged. One side of the device acts as the working electrode. For a counter electrode, a platinum coil is used. The platinum coil preferably has 10-12 turns and a wire diameter of 0.25 mm. A silver/silver chloride reference electrode is preferably used to monitor the reaction voltage. The solution is preferably purged with nitrogen for ten minutes prior to starting the electrochemistry. Nitrogen is constantly flowed into the flask during the experiment to maintain a neutral and non-oxidative environment above the solution. An oxidative potential is applied to one side of the electrode junction device, and ground to the platinum coil. A potentiostat system (e.g. Princeton Applied Research model 263A-1 potentiostat/galvanostat) is preferably used to generate the potential difference. This method oxidizes the monomers and triggers a chain reaction resulting in the formation of polymer nanowires.

A variety of substances can be used for, or in place of, nanowires including carbon nanotubes, graphene nanofilms, silicon nanowires, tin nanowires, titanium nanowires, metal oxids (zinc, magnesium, calcium, manganese, titanium, tin, and copper oxide) nanowires and nanotubes, graphene, and quantum dots. These various substances can be used for chemiresistive microelectronic sensing applications.

The PNMDs' sensitivity to both MMH and $NO_2$ was tested. The PNMDs were tested for stability, sensitivity, response time, and temperature dependence over −46° C. to +71° C. PNMDs exhibit the ability to detect and distinguish 10-300 ppm of MMH and 10-100 ppm of MON-25 within 10 minutes. PNMDs are resistant to interfering gases such as oxygen, carbon dioxide, methane, acetone, alcohol (methanol), and water, with only a slight sensitivity to ammonia. PNMDs show promising stability to shock, vibration and long-term testing. A small footprint PNMD with electronic circuitry preferably provides calibration-free operation, eliminating drift and the effects of temperature and humidity. PNMD is suitable for integration with missiles, highly reliable detection of MMH and $NO_2$, an effective early warning system for trace detection of hypergolic fuel leaks with resistance to trace interferents, vibration and mechanical perturbations. PNMDs are also suitable to operate under a wide range of temperatures and environments.

Figure 3:
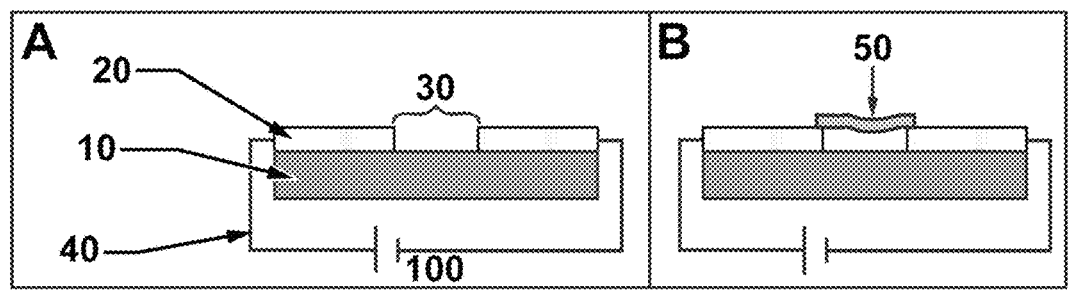
FIG. 3 is a schematic of a preferred embodiment of a PNMD sensor.

Referring now to FIG. 3, a schematic of a preferred embodiment of a PNMD is shown. This preferred embodiment preferably has at least two electrodes 20 mounted on a silicon substrate 10. The electrodes 20 are connected to a power source 100 by leads or wires 40. The electrodes 20 are preferably made of a noble metal such as gold or platinum and are separated by a gap 30 of 0.5 μm (500 nm) to 4.0 μm (4000 nm). The gap 30 is preferably 2.0 μm (2000 nm). The electrodes 20 are preferably electrically connected by a polymer nanowire or carbon nanotube 50 of diameter 30-150 nm and length 2-10 μm.

Figure 2B:
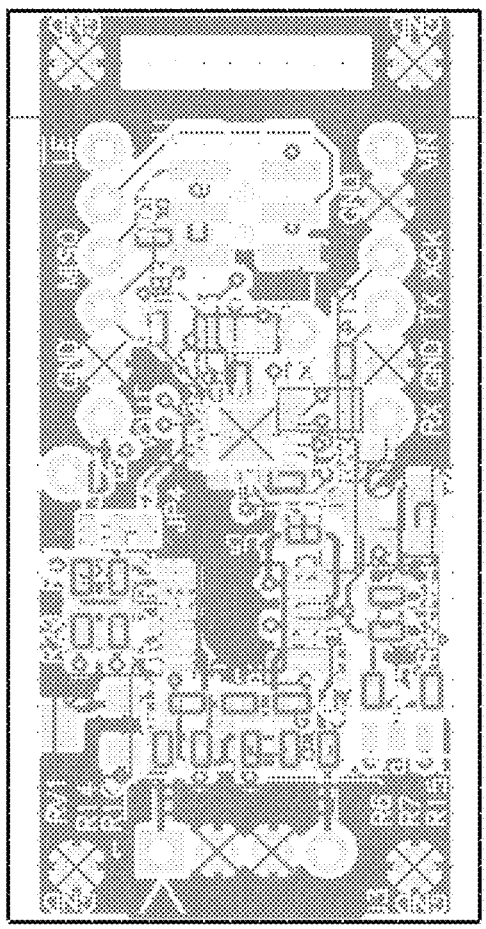
FIG. 2B is a schematic of a preferred embodiment of a layout of the circuit board assembly in FIG. 2.
Figure 2:
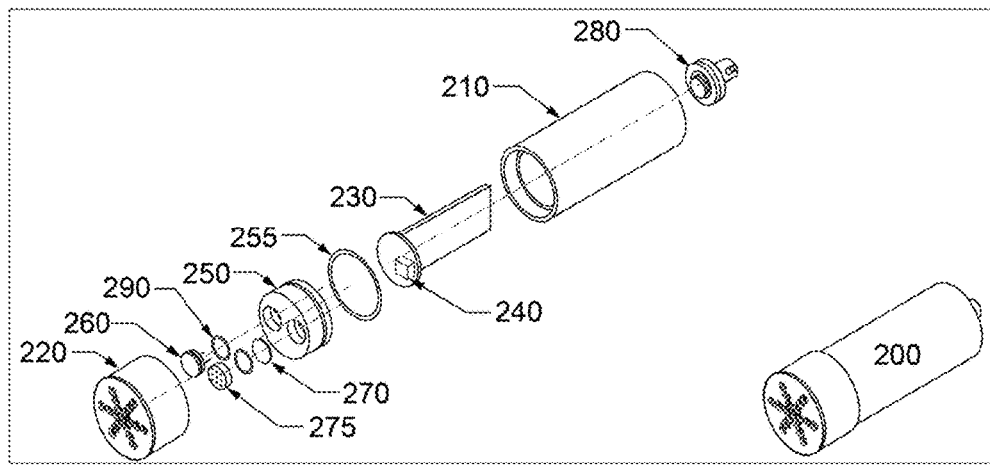
FIG. 2 is an exploded view of a preferred embodiment of a polymer nanowire microelectronic hypergolic leak detector (PNMD) sensor housing.

Referring to FIG. 2, an exploded view of a preferred embodiment of the sensor assembly 200 for the PNMD is shown. The sensor assembly preferably has a main housing 210 and a protective cap 220 to contain a circuit board assembly 230 with a PNMD sensor (or array of sensors) 240 mounted thereon. A sensor insert plug 250 and O-ring 255 preferably separate the PNMD sensor 240 and circuit board assembly 230 from a temperature sensor 260. The sensor insert plug 250 preferably comprises a member 270 and membrane retainer 275. A MIL standard connector 280 is mounted to housing 210 to connect the sensor assembly 200 to data and/or power sources (not shown).

Figure 2A:
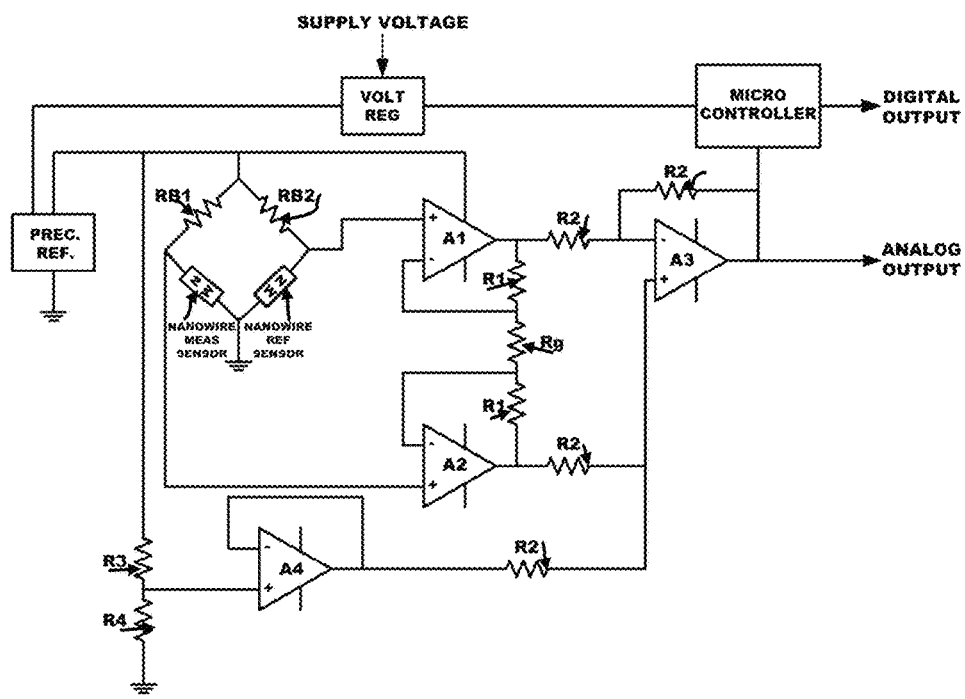
FIG. 2A is a schematic of a preferred embodiment of a circuit diagram for the circuit board assembly in FIG. 2.

FIGS. 2A and 2B show schematics of the preferred embodiment for the circuit board assembly 230. In the FIG. 2A, the circuit 230 used for the nanowire sensors has a balanced bridge design with one sensor for reference and a second one for measurement. The bridge is formed by two nanowire sensors 240 and two precision resistors (RB1 and RB2). These fixed resistors are by design nearly equal to the room temperature resistance of the nanowire sensors. A precision 3-volt reference source i drives the bridge. This voltage source is powered by a voltage regulator to minimize the dependency on the supply voltage. A differential voltage is formed at the two nodes of the bridge, which are connected to an instrumentation amplifier formed by amplifiers A1, A2 and A3. The gain of the instrumentation amplifier is controlled by a single resistor, Rg, and is equal to G=1+(2R1/Rg). Initially, the gain (G) of this circuit is set to 1 due to the high sensitivity of the nanowire sensors to the presence of the gas.

Although resistors RB1 and RB2 are selected to balance the bridge as well as possible, there is inevitably some small residual differential voltage. The nominal output of the instrumentation amplifier can be set by adjusting the offset input that is supplied by amplifier A4. This is a unity-gain buffer amplifier that sets the offset voltage based upon the resistive divider formed by R3 and R4. This resistive divider is driven by the precision reference source so that the offset will track any small changes in the reference source as temperature is varied. The final output of the instrumentation amplifier is provided as an analog output for data logging purposes. It is also provided to the input of an ADC within the on-board microcontroller, where it can be digitized, processed, and sent out through a serial communication port. The entire circuit is designed on a circuit board 230 that preferably measures 0.9 in.×1.7 in., which includes space for some connectors in order to make the testing more convenient. FIG. 2B shows the layout of main circuit board.

Figure 10:
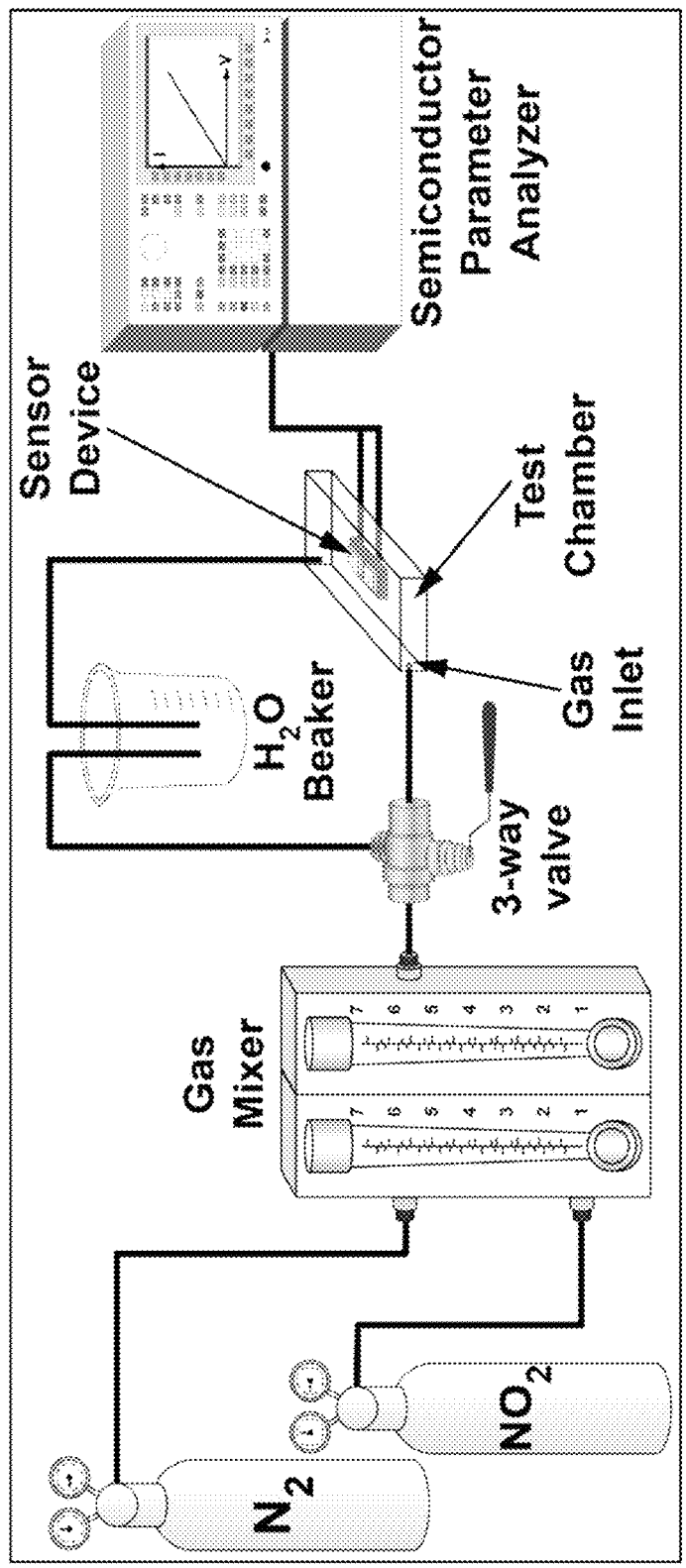
FIG. 10 is a schematic of a test setup to measure I-V curves of a nanowire sensor.

The simplest configuration of the nanowire sensor is a resistive junction composed of two solid state electrodes between which conducting polymer materials are grown. FIG. 10 shows a schematic test setup for measuring I-V curves of a nanowire sensor. The electron transport properties of the sensor change upon exposure to analytes such as $CO_2$, MMH, $NO_2$ or bio-molecules. The equilibrium driven analyte binding interactions (van der Waals and/or dipole-dipole in nature) with nanowires change in electronic density and current flow of nanowires. The current-voltage curves of a nanowire sensor are measured before and after exposing the sensor to a target analyte ($CO_2$, MMH, $NO_2$ or biomolecues). The change in conducting current (before and after) of the nanowire sensor is directly proportional to the concentration of the exposed analyte. Therefore, by measuring the change in conducting current before and after the sensor is exposed to an analyte, the concentration of the target analyte can be determined. This calibration can be stored locally in the sensor assembly or in some other storage medium for later look-up.

Figure 11:
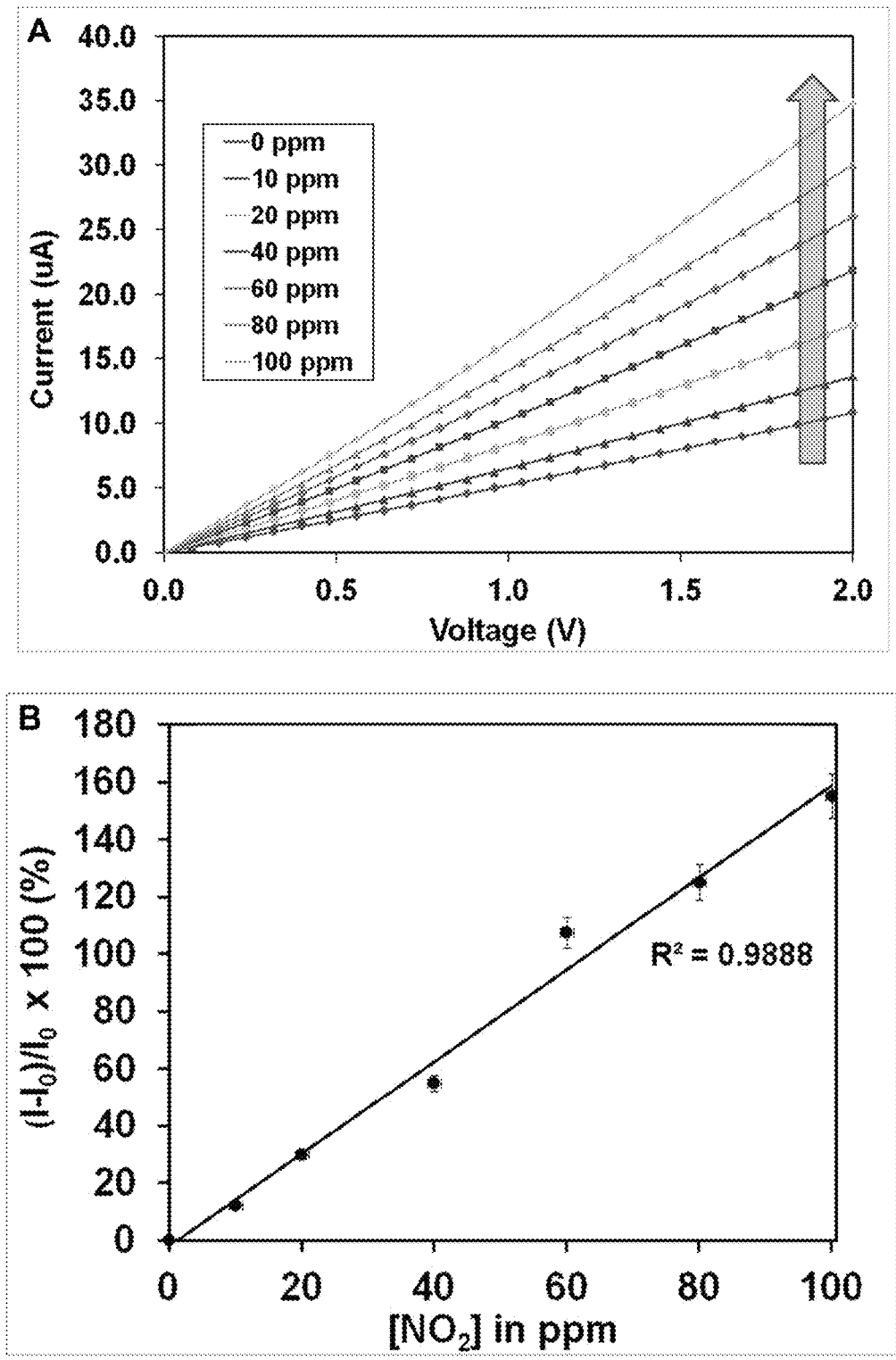
FIG. 11 are (A) a graph of the PNMD sensor with increasing $NO_2$ concentrations at room temperature (the arrow indicates the direction of change in signal); and (B) a graph of sensor response as a function of $NO_2$ concentration up to 100 ppm. The error bars (where visible) indicate ±5% of the value. $R^2$ indicates the regression value for the linear trend line.
Figure 13:
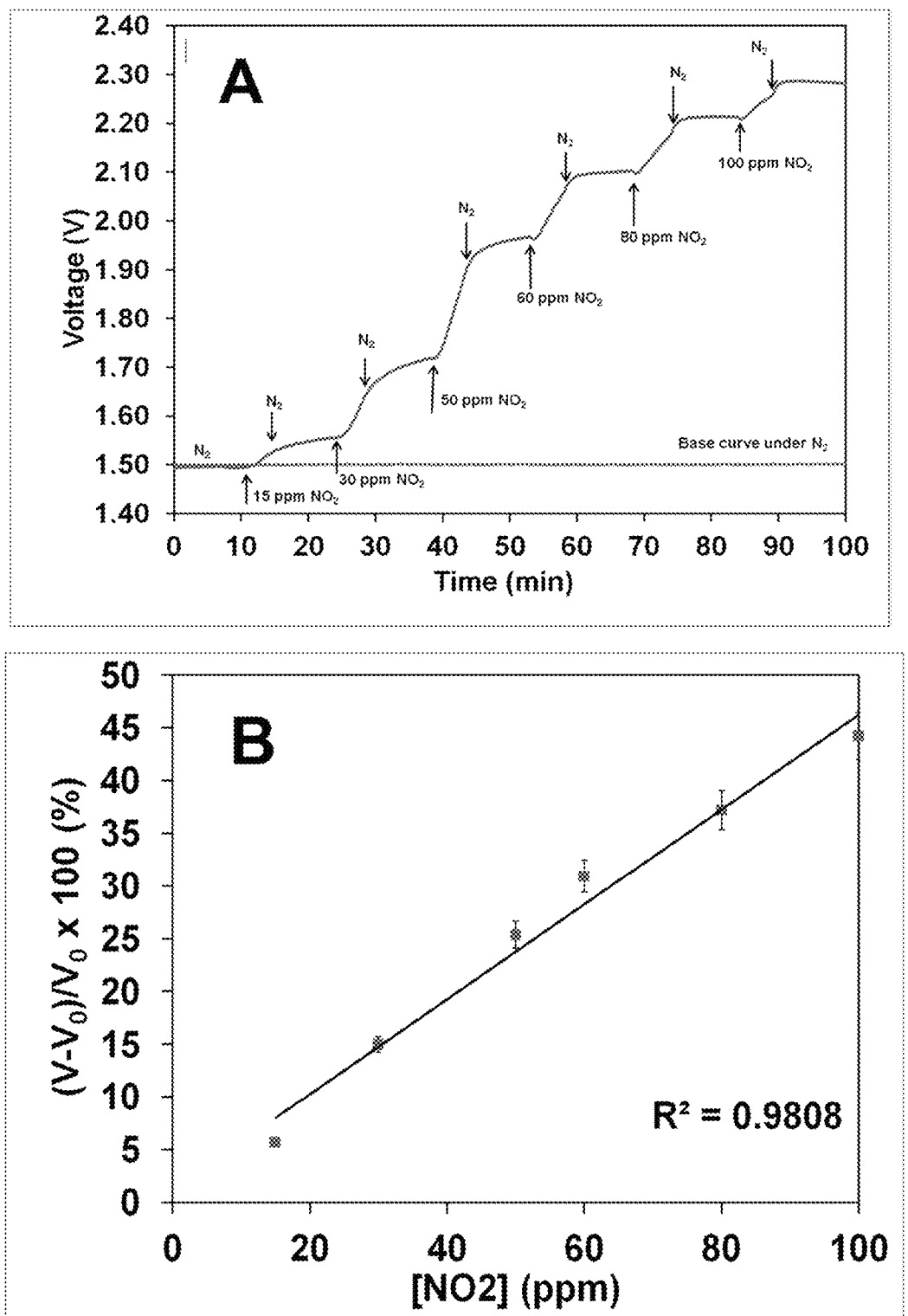
FIG. 13 are (LEFT) Signal response versus time (V-t) plot for $NO_2$ sensing by PNMD sensor tested with a breadboard device. The flat line indicates the base curves of the sensors when exposed to an $N_2$ (gas stream) alone. The other line graphs the sensor response to various concentrations of $NO_2$ (0 to 100 ppm) at 40° C. (Right) The percent change (triplicate measurements) in sensor response as a function of $NO_2$ concentration. The error bars (where visible) indicate ±5% of the value. $R^2$ indicates the regression value for the linear trend line.

PNMD sensors in the presence of MMH and $NO_2$ at temperatures of −46° C., 0° C., 23° C., 40° C. and 71° C. in dry nitrogen ($N_2$) were tested. First, the PNMDs were tested for detecting $NO_2$ gas. The sensor signal responses were measured as current-voltage (I-V) curves and voltage-time (V-t) plots with an Agilent semiconductor parameter analyzer and a breadboard device (FIGS. 11 and 13). The I-V curves plotted with the Agilent semiconductor parameter analyzer showed that the PNMDs responded significantly when exposed to $NO_2$. The device current increased in positive direction with increasing $NO_2$ concentrations (0-100 ppm) and followed a linear trend line. Similar sensor response behavior was observed at all measured temperatures.

Figure 12:
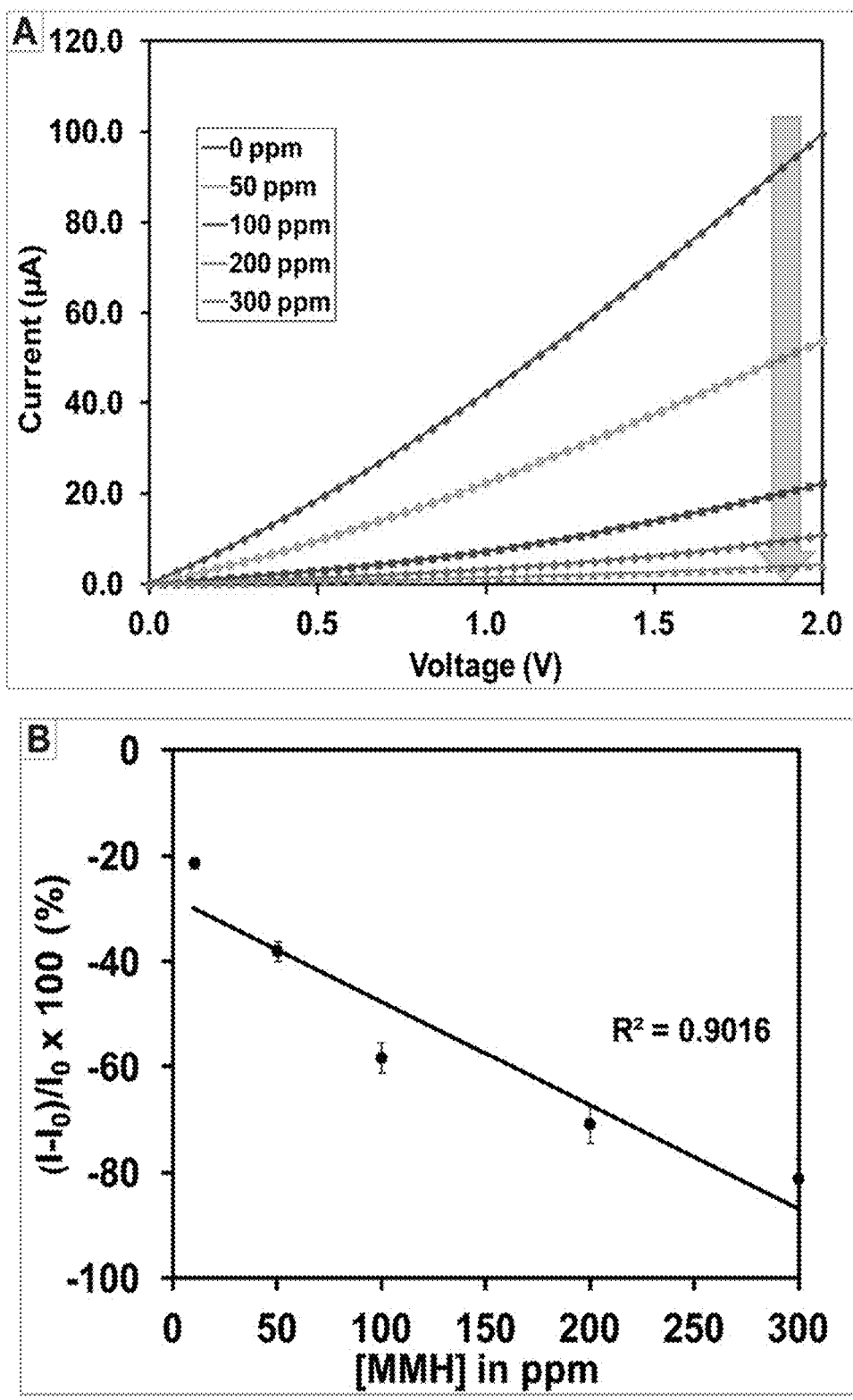
FIG. 12 are (A) a graph of I-V curves of the PNMD sensor with increased MMH concentrations at 23° C. The arrow indicates the direction of change in signal. (B) Change in sensor response as a function of MMH concentration up to 300 ppm. The error bars (where visible) indicate ±5% of the value. $R^2$ indicates the regression value for the linear trend line.

FIG. 12A shows I-V curves for detecting MMH at 23° C. measured with an Agilent semiconductor parameter analyzer. The PNMDs show significant response when exposed to MMH, and the device current decreased linearly as the concentration (0-300 ppm) of MMH increased (FIG. 12A) and followed a linear trend line (FIG. 12B). Similar sensor response was observed at other measured temperatures mentioned above.

FIG. 13 shows a representative voltage-time (V-t) plot measured by using a breadboard device at 40° C. for sensing $NO_2$. FIG. 13B shows that PNMD response increased to positive direction with increasing $NO_2$ gas concentration (0-100 ppm) due to oxidizing nature of $NO_2$. Similar $NO_2$ sensing responses were observed for the PNMDs at all measured temperatures.

Figure 14:
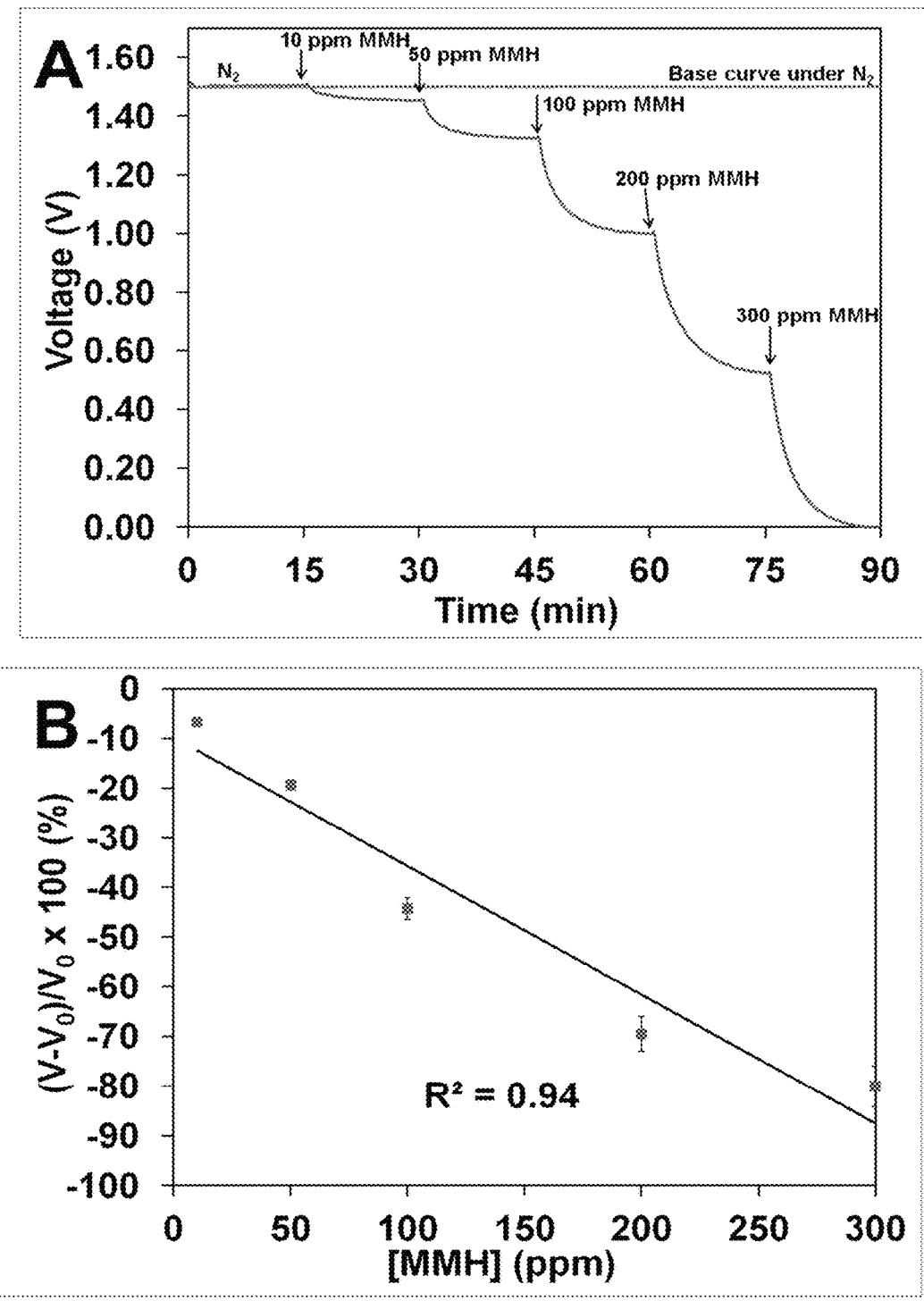
FIG. 14 are (LEFT) a graph showing signal response versus time (V-t) plot for MMH sensing by PNMD sensor tested with a breadboard device. The flat line indicates the base curves of the sensors when exposed to $N_2$ (air) alone. The other line graph indicates the sensor response to various concentrations of MMH (0 to 300 ppm) at 40° C. (Right) The percent change (triplicate measurements) in sensor response as a function of MMH concentration. The error bars (where visible) indicate ±5% of the value. $R^2$ indicates the regression value for the linear trend line.

For sensing MMH (0-300 ppm), the sensor response (V) increased to negative direction with increasing concentration of MMH because of the reducing nature of MMH. FIG. 14 shows a representative V-t graph and a linear trend line plot at 40° C. for sensing MMH. Similar MMH sensing responses were observed for the PNMDs at all measured temperatures.

Figure 15:
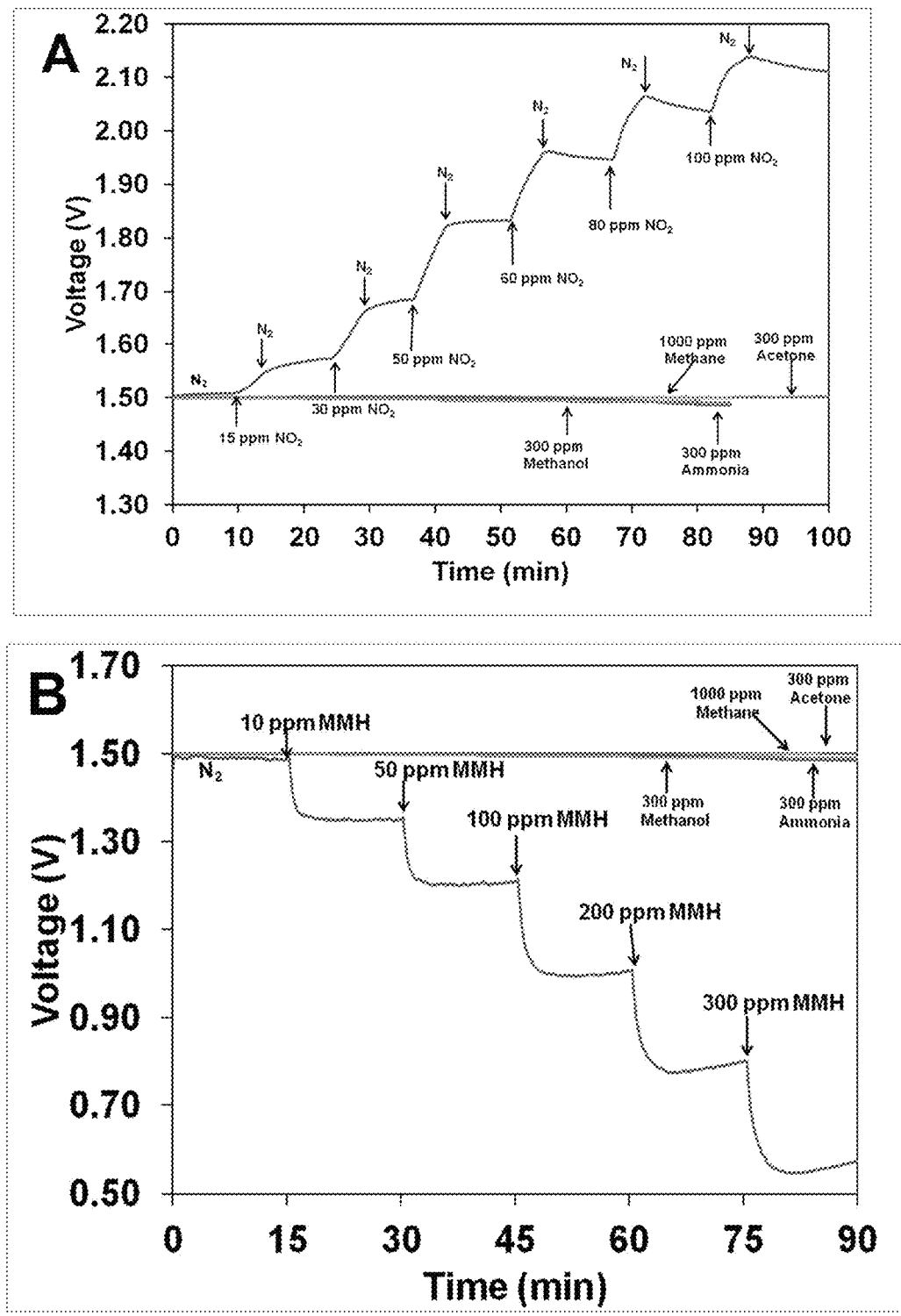
FIG. 15 are graphs of PNMD performance detecting $NO_2$ (left graph) and MMH (right graph) emphasizing the responses of $NO_2$ and MMH compared to the interfering gases. (Left) 0-100 ppm $NO_2$ response and (right) 0-300 ppm MMH response plotted with the response from the interfering gases.

PNMD sensors could indicate trace leaks (≤50 ppm) of both MMH and $NO_2$ within minutes (<5 minutes) with high reliability, minimal cross-sensitivity, and minimal response to trace interference gases (FIG. 15). PNMDs show very promising long term operational stability (measured over six months), shelf-life, and tolerance to shock, and vibration.

Figure 5:
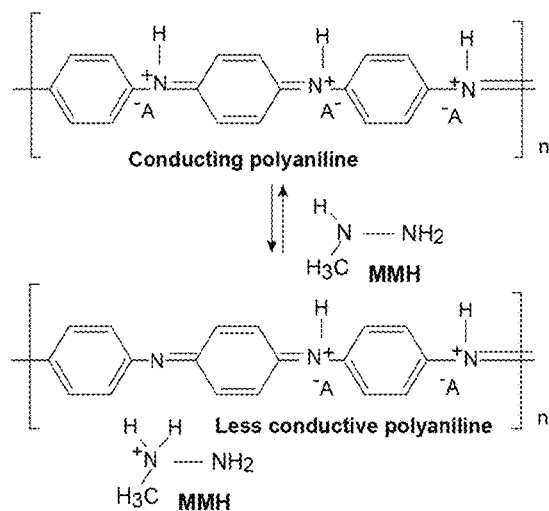
FIG. 5 is a diagram showing MMH interaction decreases the conductivity of polyaniline because of the reducing nature of MMH.
Figure 6:
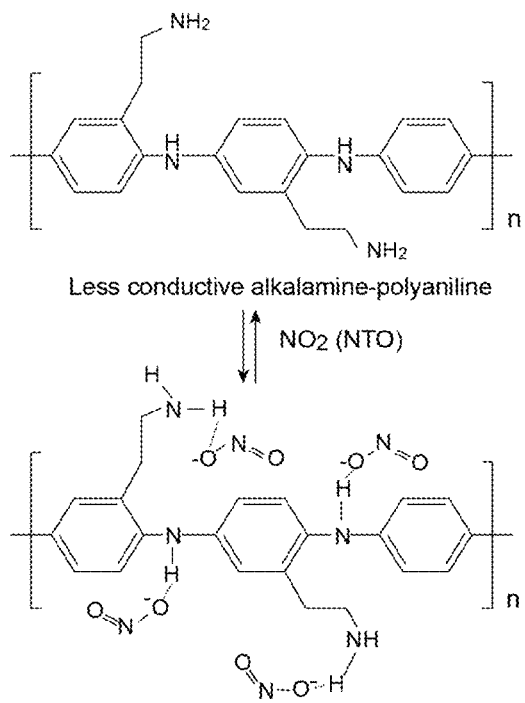
FIG. 6 is a diagram showing $NO_2$ interaction increases the conductivity of alkylamine functionalized polyaniline because $NO_2$ is a strong oxidizing agent.
Figure 7:
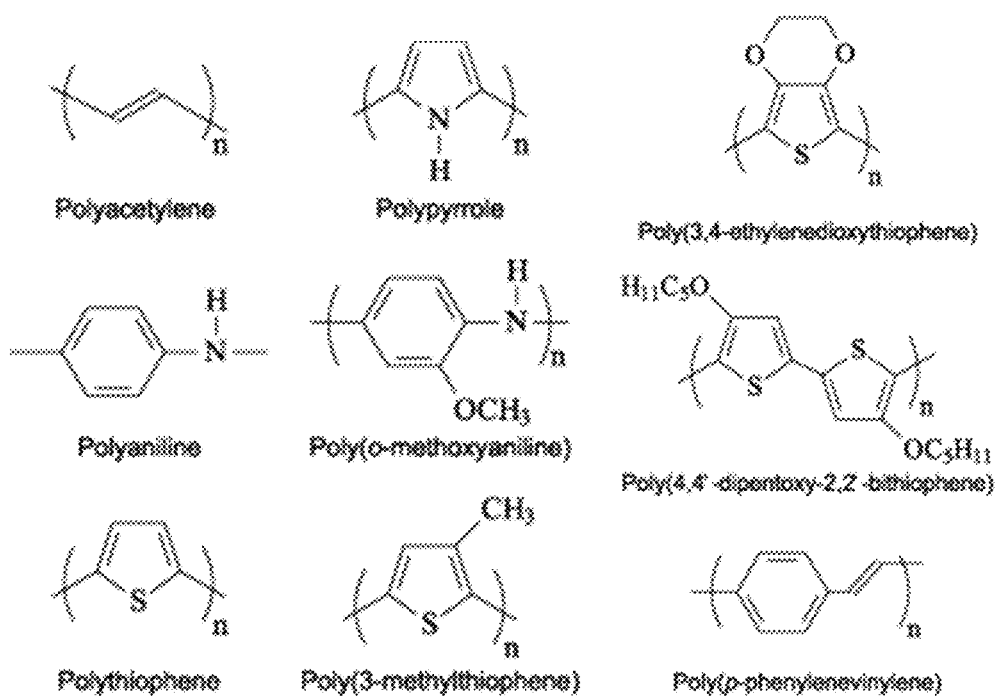
FIG. 7 is a diagram of chemical structures of other conducting polymers that can be used for the development of PNMD (MMH and $NO_2$ sensor)
Figure 8:
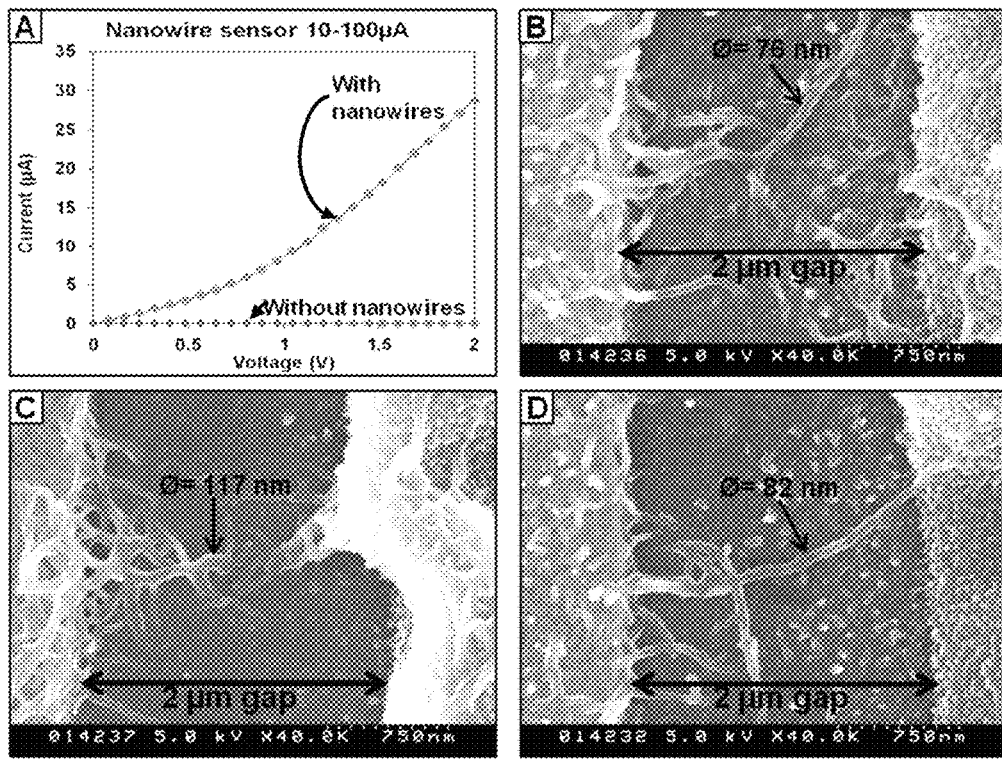
FIG. 8 is an (A) graph of an I-V curve of a sensor device before and after nanowire growth; (B-D) are SEM images of nanowires grown at a 2 µM gap of the device.

Chemical structure of polyaniline and its interaction with MMH are shown in FIG. 5. In this figure, the common polyaniline is used to detect MMH. FIG. 6 shows the chemical structure of functionalized polyaniline and its interaction with $NO_2$. The novel process for the growth of polymer nanowires and the fabrication of both MMH and $NO_2$ sensors described herein was used.

Carbon Dioxide ($CO_2$) Monitoring.

Figure 16:
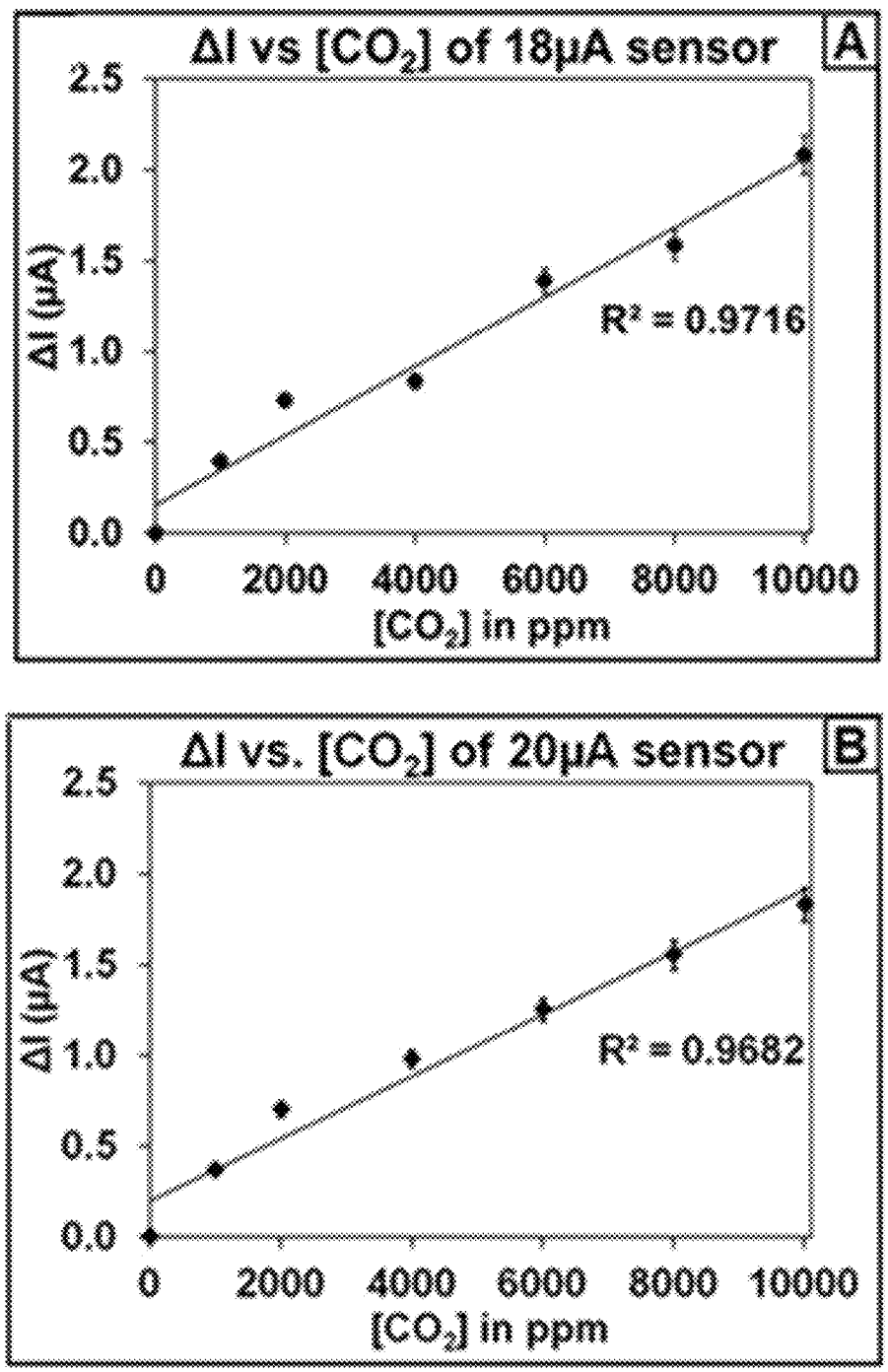
FIG. 16 are response plots as a function of $CO_2$ concentrations up to 10,000 ppm of two nanowire sensors (A and B). Each point is the average of three measurements, and the error bars (where visible) indicate ±5% of the value. $R^2$ indicates the regression value for the trend line.

Through customization of polymer nanowires or carbon nanotubes by chemical synthesis, a nanowire or carbon nanotube sensor for detecting the environmental and subsurface $CO_2$ has been developed. The customized nanowire or carbon nanotube sensors detect $CO_2$ reversibly in the 0 ppm to 10,000 ppm range (FIG. 16) with response time of 2 minutes and reversing within 30 minutes in the temperature range of 10° C. to 60° C. and over 0% to 80% relative humidity. Using a DC intensity measurement system, $CO_2$ concentrations as low as 25 ppm were detected.

Figure 22:
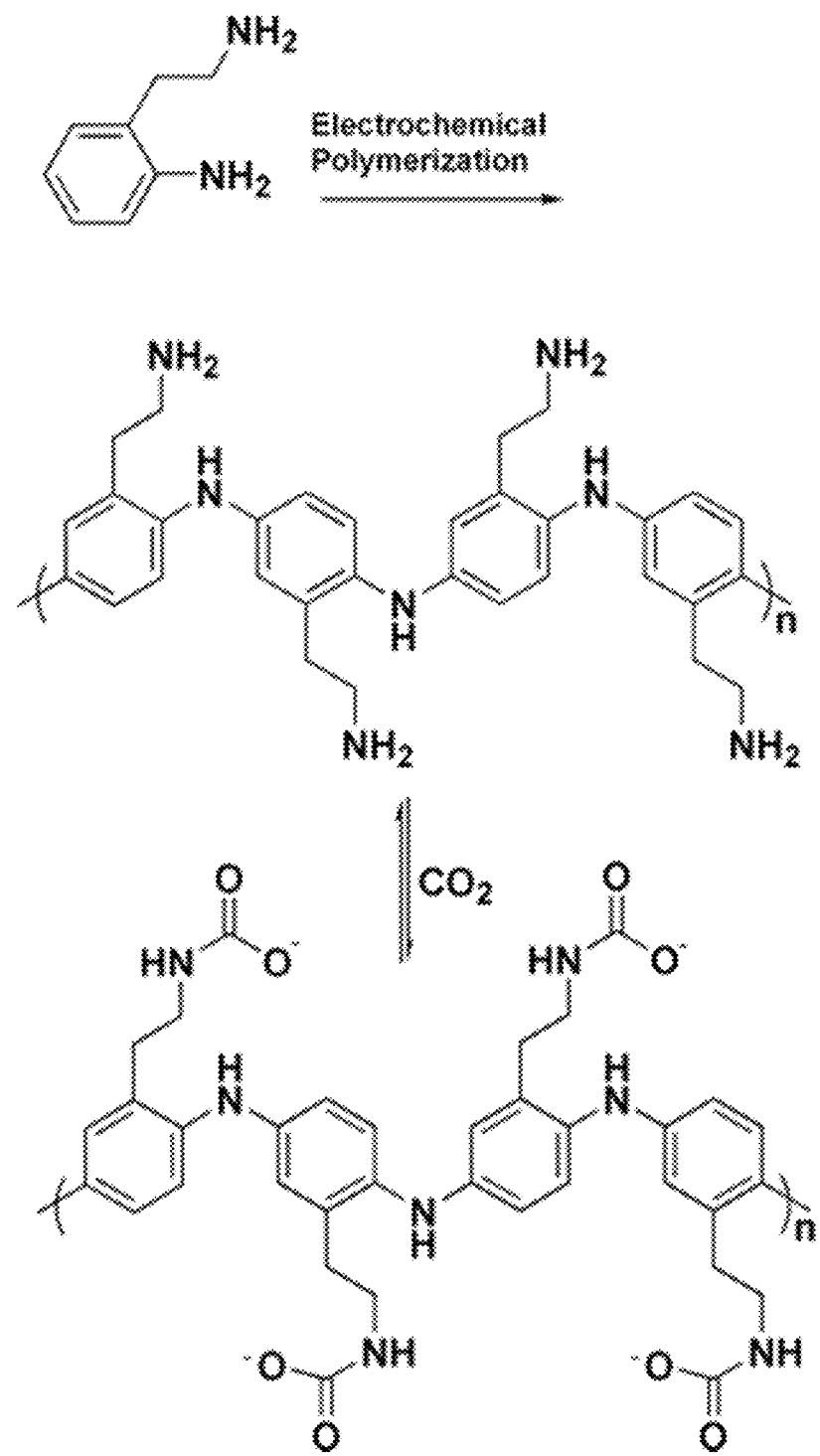

Alkyl amine-modified polymer nanowires for selective and sensitive $CO_2$ detection were developed. First, alkylamine functionalized aniline monomer was synthesized by chemical reactions and this monomer was used to create alkyl amine-modified polymer nanowires using template-free electrochemical method. The chemical structure and its interaction with $CO_2$ are shown in FIG. 22. The formation of the carbonate upon $CO_2$ interactions with the amine groups of the nanowire imparts this selectivity. To the best of the applicants' knowledge, the amine-modified aniline monomer is a unique compound. The formation of the carbonate is a reversible reaction. Thus, the sensor is reversible and can detect both increases and decreases in $CO_2$ levels.

In addition, the novel growth process of creating polymer nanowires disclosed herein is unique because of the following reasons: 1. Six different electrolyte systems (formic acid, acetic acid, perchloric acid, hydrochloric acid, phosphoric acid and nitric acid) have been investigated with varying concentrations (0.2-1.0 M) in deionized water for the growth of polymer nanowires using three-step electrochemical method. These electrolytes offer specific counter ions, ionic strength, polarity, and acid strength (pKa) that play a critical role during nanowire growth.

Both electrolyte system and its concentration are optimized to achieve high quality polymer nanowires with diameters ranging from 30 nm to 150 nm, length ≥2 µm and highly porous nano-network morphology, resulting in high surface area, highly reactive sites and enhanced response and sensitivity for detecting $CO_2$. It appears that 0.4-0.6 M nitric acid is the best electrolyte media for the growth of these amine functionalized polyaniline nanowires.

The concentration effect of amine functionalized aniline monomer (0.1-1.0 M) was investigated in an electrolyte system (0.4-0.6 M nitric acid). The optimized monomer concentration was found to be 0.2-0.4 M in nitric acid (0.4-0.6 M) electrolyte system to obtain the above mentioned high quality polymer nanowires.

The quality of polymer nanowires was further optimized by applying very low-level current (12-50 nanoampere) and slow growth mechanism over a period of time (4-6 hours). The high quality polymer nanowires obtained in this process mentioned above were confirmed by scanning electron microscope (SEM) analysis, current-voltage (I-V) measurements and evaluating $CO_2$ sensor performance. This novel process was used for the fabrication of other sensors.

Figure 9:
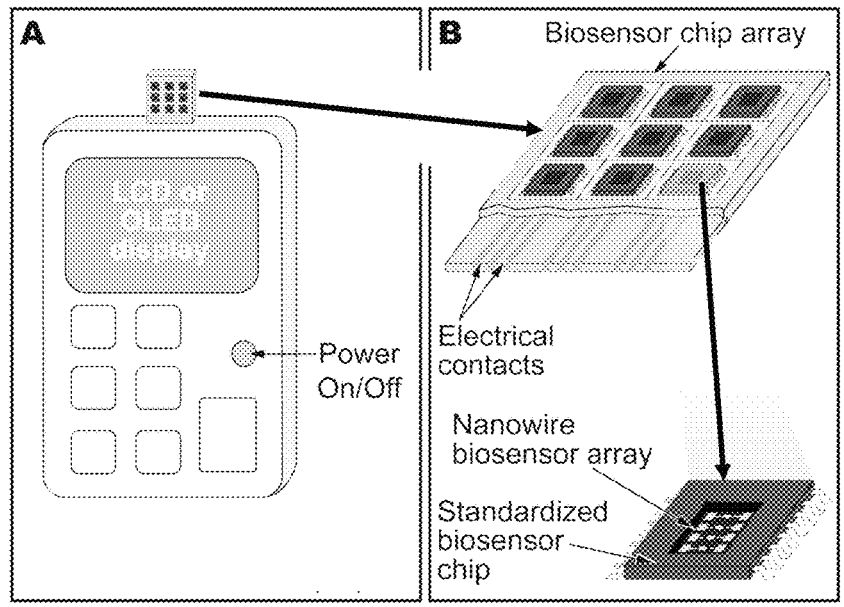
FIG. 9 is a schematic of (A) a preferred embodiment of a portable handheld bio-sensor for point of care early diagnosis of disease and (B) a sensor array chip.

Detection of Disease Biomarkers. The present invention can be used for detection of disease biomarkers. Referring now to FIG. 9, a general schematic for a biosensor for use in early diagnostics is shown. A nanowire biosensor array is mounted on a bionsensor chip. One or more chips are mounted on a card with electrical contacts. Each of the chips can be designated for detection of a different disease biomarker (for an expanded survey of tests for, e.g. cancers, Alzheimer's (see below), Parkinson's, Hepatitis, Cardiac disease, etc.) or each of the chips can be designated for the same disease biomarker (for additional accuracy). The card is then inserted into the hand-held device in FIG. 9A for analysis of the data collected from the biosensor chips and card.

Figure 17:
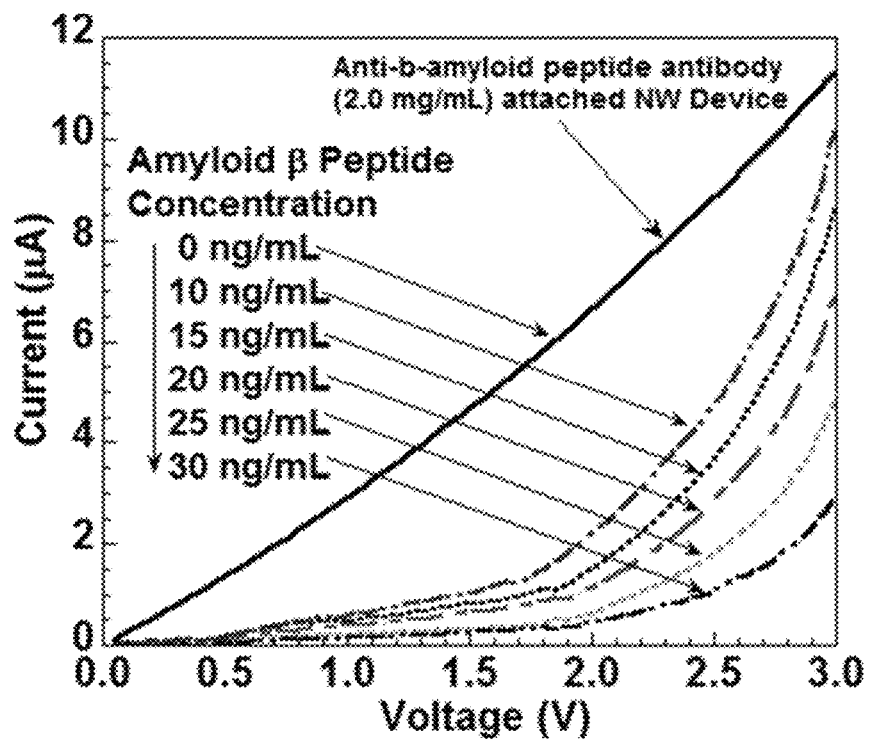
FIG. 17 is a graph of I-V curves of an anti-$A\beta_{42}$-modified nanowire device exposed to PBS solutions spiked with $A\beta_{42}$.

Another preferred embodiment is a polymer nanowire or carbon nanotube platform-based sensor for early diagnosis of Alzheimer's disease (AD) by detecting AD-associated biomarkers. Conducting polymers or carbon nanotubes modified with covalently attached antibodies specific to different AD biomarkers such as different forms of Aβ (monomers and oligomers) as capture and transducing agents for an electrochemical-based biosensor were used in the sensor. Nanowire or nanotube devices detect 36 pM for the Aβ oligomer and sub-pM for the Aβ monomer. This is approximately three orders of magnitude better than what can be achieved using the same antibodies in enzyme-linked immunosorbent assay (ELISA) or blot tests for Aβ detection (1-10 nM). Antibodies attached to nanowires or nanotubes via amide coupling with N-hydroxysuccinimide. Standard current-voltage (I-V) curves were obtained when the anti-Aβ42 sensors were tested with a semiconductor parameter analyzer. FIG. 17 shows the I-V curves of an anti-Aβ42 peptide antibody-attached sensor exposed to varying concentrations of Aβ42 in phosphate buffered saline (PBS) solution for 5 min. at each concentration. A significant change in the I-V curve of the anti-Aβ42 peptide antibody-attached sensor was observed after successive exposures of Aβ42. All sensors responded to the introduction of Aβ, as expected. This antibody-based nanowire or nanotube sensor exhibited much higher sensitivity than the ELISA and Western-blot tests.

Figure 19:
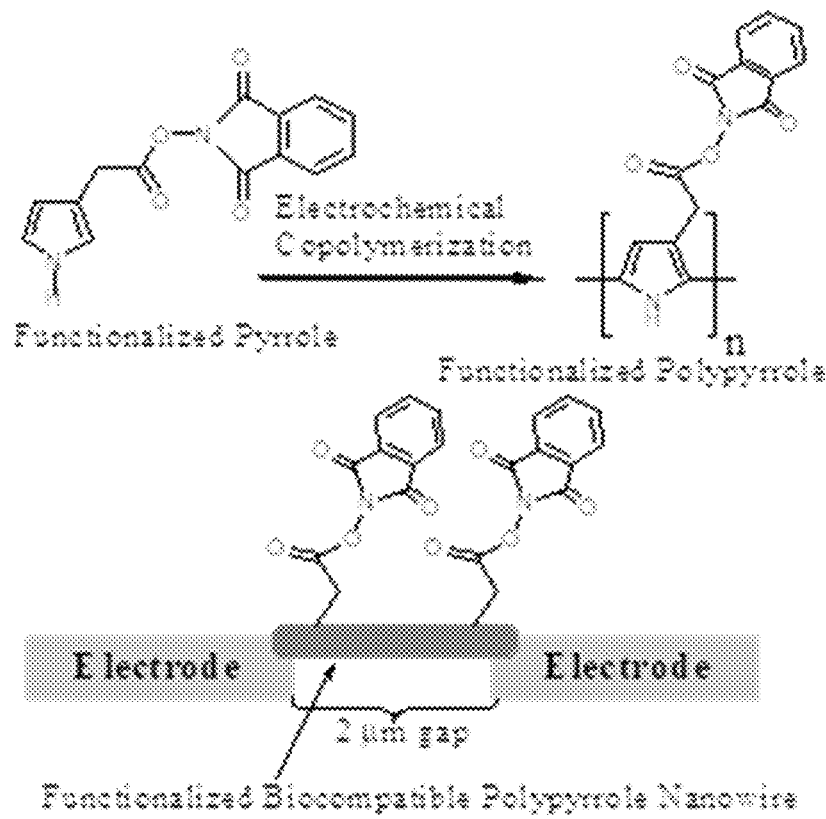
FIG. 19 is a diagram of chemical structure of functionalized biocompatible polypyrrole for biosensor development.
Figure 20:
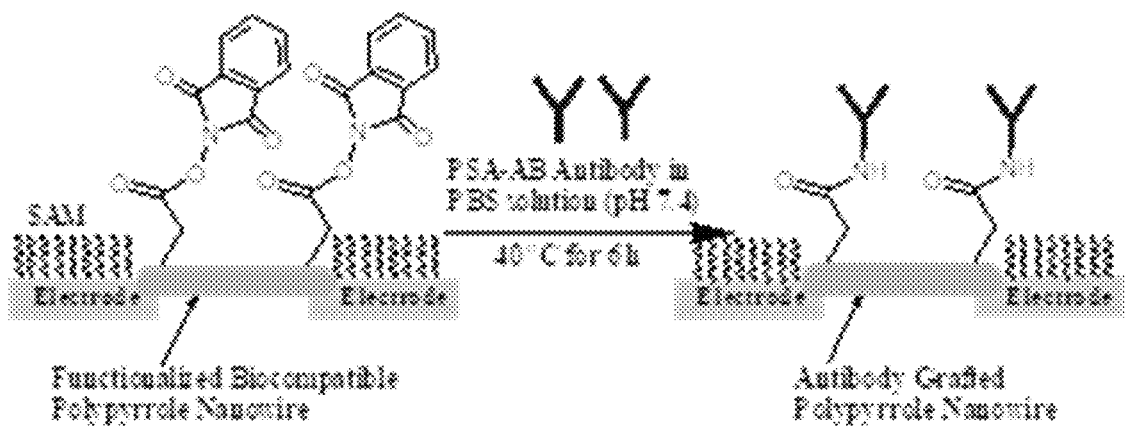
FIG. 20 is a diagram of conjugation of antibody to functionalized biocompatible polypyrrole.
Figure 21:
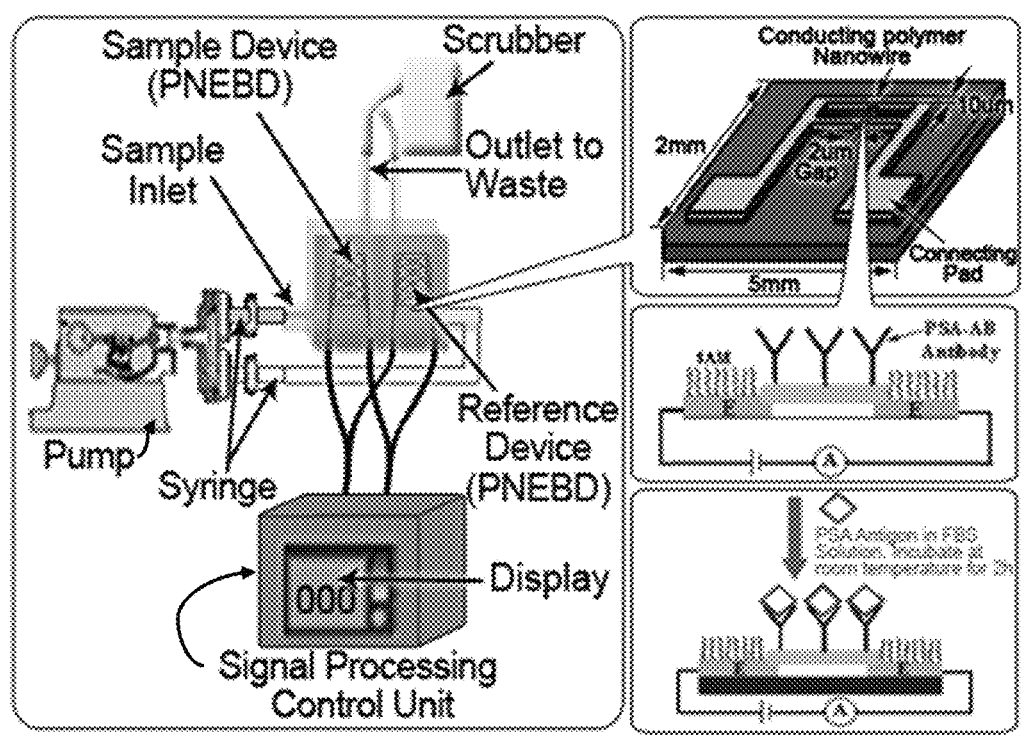
FIG. 21 is a schematic of interaction of antibody with corresponding disease biomarker antigen or protein for detecting disease; and, FIG. 22 is a diagram of a reversible interaction of $CO_2$ with the alkylamine ($R—NH_2$) of the conducting polymers to form carbonate ($R—NHCO_2$).

Referring now to FIG. 19, for the development of biosensors to detect Alzheimer's disease (AD) or cancers, N-hydroxyphathalo-succinimide or N-hydroxysuccinimide functionalized pyrrole monomer was synthesized and created N-hydroxyphathalo-succinimide or N-hydroxysuccinimide functionalized polypyrrole nanowires by electrochemical method. Referring to FIG. 20, antibody conjugation followed the above synthesis. FIG. 21 then shows the interaction with biomarkers for disease detection.

Figure 18:
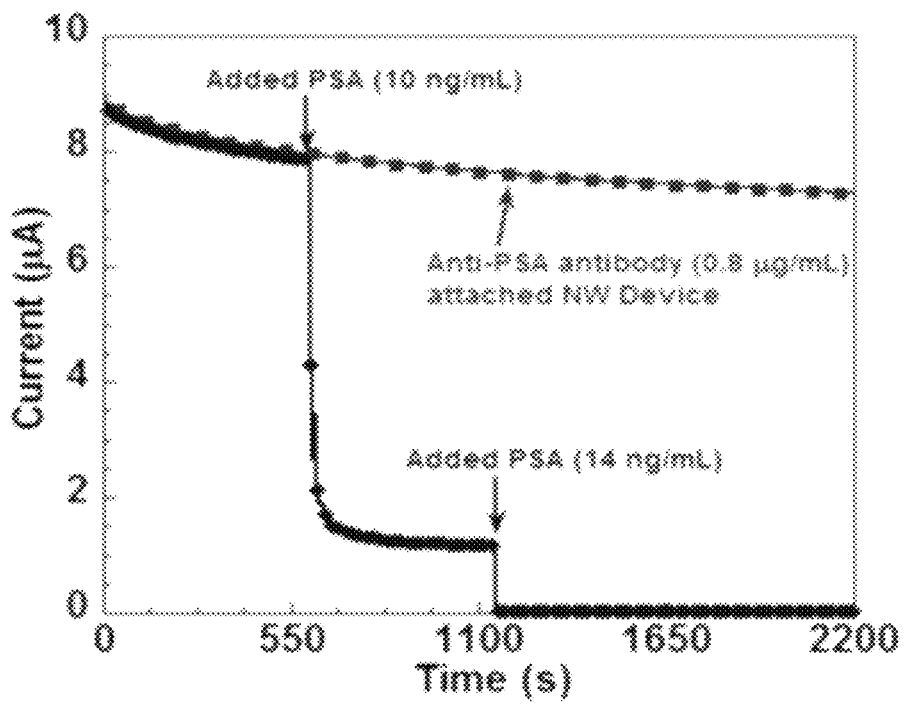
FIG. 18 is a graph of current versus time plots of an anti-PSA-antibody attached nanowire biosensor exposed to PSA antigen with 0, 10 and 14 ng/ml.

A polymer nanowire or carbon nanotube sensor device for the detection of prostate cancer biomarker PSA (prostate specific antigen) is another preferred embodiment. The response time of nanowire- or nanotube-based sensors was evaluated by detecting current changes as a function of time. FIG. 18 shows the current vs. time response for a nanowire or nanotube sensor functionalized with anti-PSA antibodies that was exposed to a constant bias of 2.5 V. A much more significant change in current was observed when small concentrations of the antigen were added. In all cases, the response occurred and stabilized within a few minutes.

A template-free, site-specific electrochemical approach to the precise fabrication of individually addressable polymer nanowire or carbon nanotube microelectronic electrode junction devices has been developed. A library of different polymer nanowires or carbon nanotubes can be incorporated into an array format by addressing each individual junction electrochemically in the presence of a particular electroactive monomer. For example, a list of preferable nanomaterials for different sensors follows:

| Sensor Type | Nanomaterials currently in use | Additional preferable nanomaterials |
|---|---|---|
| $CO_2$ Sensor | Amine functionalized polymer nanowires | Amine functionalized carbon nanotubes |
| $NO_2$ and MMH Sensors | Functionalized polyaniline nanowires | Modified single wall carbon nanotubes |
| Alzheimer's Disease (AD) Sensor | N-Hydroxy succinimide functionalized polymer nanowires followed by conjugation with AD proteins and biomarkers | N-Hydroxy succinimide functionalized single wall carbon nanotubes followed by conjugation with AD proteins and biomarkers |

It has been demonstrated in this disclosure that the excellent performance of the modular nanowire or nanotube microelectronic sensors in terms of their high sensitivity and their fast response for detecting toxic chemicals, gases and biomarkers are useful. These results demonstrate the versatility of modular nanowires or nanotubes microelectronic sensor technology for chemical and biological sensor applications.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether flow control or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A modular chemiresistive sensor system comprising at least two noble metal electrodes, a power source and a circuit board for measuring current and/or voltage between the at least two noble metal electrodes, the at least two noble metal electrodes mounted on a silicon substrate and separated by a gap of 0.5 to 4.0 µm; and
    a polymer nanowire, said polymer nanowire having a porous nano-network, spanning the gap and connecting the at least two noble metal electrodes
    said system including a processor configured to display the measured current and/or voltage between the at least two noble metal electrodes as a concentration of a compound selected for detection.

2. The modular chemiresistive sensor system of claim 1 where the porous polymer nanowire has a diameter less than 150 nm.

3. The modular chemiresistive sensor system of claim 1 where the porous polymer nanowire comprises at least one of the following: aniline, pyrrole, thiophene or ethylenedioxythiophene.

4. The modular chemiresistive sensor system of claim 1 where the porous polymer nanowire comprises at least one of the following: amine functionalized 2-(2-aminoethyl) aniline, amine functionalized pyrrole, thiophene or ethylenedioxythiophene.

5. The modular chemiresistive sensor system of claim 1 where the porous polymer nanowire comprises covalently attached antibodies specific to Alzheimer's disease biomarkers.

6. The modular chemiresistive sensor system of claim 1 where the porous polymer nanowire comprises covalently attached antibodies specific to various cancer biomarkers.

7. The modular chemiresistive sensor system of claim 1 where the polymer nanowire comprises anti-Aβ peptide antibodies.

8. The modular chemiresistive sensor system of claim 5 where the antibodies are attached to the porous polymer nanowire via amide coupling with N-hydroxysuccinimide.

9. The modular chemiresistive sensor system of claim 1 where the porous polymer nanowire comprises anti-PSA antibodies.

10. A modular chemiresistive sensor comprising at least two noble metal electrodes, a power source and a circuit board, said at least two noble metal electrodes mounted on a silicon substrate and separated by a gap of 0.5 to 4.0 µm;
   a porous polymer nanowire spanning the gap and connecting the at least two noble metal electrodes;
   where the circuit board comprises a processor and data storage, said processor configured to measure current and voltage values between the at least two noble metal electrodes and compare the current and voltage values with current and voltage values stored in the data storage, said current and voltage values indicating particular concentrations of a pre-determined substance.

11. The modular chemiresistive sensor system of claim 10 where the porous polymer nanowire is functionalized to selectively determine the presence of nitrogen dioxide.

12. The modular chemiresistive sensor system of claim 10 where the porous polymer nanowire is functionalized to selectively determine the presence of monomethyl hydrazine.

13. The modular chemiresistive sensor system of claim 10 where the porous polymer nanowire is functionalized to selectively determine the presence of Alzheimer's disease biomarker.

14. The modular chemiresistive sensor system of claim 10 where the porous polymer nanowire is functionalized to selectively determine the presence of Aβ peptides.

15. The modular chemiresistive sensor system of claim 10 where the porous polymer nanowire is functionalized to selectively determine the presence of prostate specific antigen.

16. The modular chemiresistive sensor system of claim 10 where the porous polymer nanowire is functionalized to selectively determine the presence of carbon dioxide.

17. The modular chemiresistive sensor system of claim 10 where the porous polymer nanowire is selected from the group consisting of polyacetylene, polypyrrole, poly(3,4-ethylenedioxythiophene), polyaniline, poly(o-methoxyaniline), poly(4,4'-dipentoxy-2,2'-bithlophene), polythiophene, poly(3-methylthiophene), and poly(p-phenylenevinylene).

18. The modular chemiresistive sensor system of claim 1 wherein said chemiresistive sensor system is sensitive to concentrations of monomethyl hydrazine and/or $NO_2$ but insensitive to oxygen, carbon dioxide, methane, acetone, methanol, and water.

19. The modular chemiresistive sensor system of claim 1 where the polymer nanowire comprises an alkyl amine-modified polymer nanowire synthesized from amine-modified aniline monomer, said amine modified nanowire providing a modular chemiresistive sensor system suitable for sensing quantities of $CO_2$.

20. The modular chemiresistive sensor system of claim 1 wherein the circuit board comprises a 3 volt reference source and a balanced bridge comprising two resistors of a resistance equal to that of the nanowires.

21. The modular chemiresistive sensor system of claim 18 wherein the polymer nanowire or carbon nanotubes are modified by amide coupling to covalently bind Aβ monomers or oligomers, said modular chemiresistive sensor system suitable for quantitatively detecting Alzheimer-associated biomarkers.

* * * * *

UNITED STATES PATENT AND TRADEMARK OFFICE
CERTIFICATE OF CORRECTION

PATENT NO. : 9,896,772 B2  
APPLICATION NO. : 14/658034  
DATED : February 20, 2018  
INVENTOR(S) : Maksudul M. Alam et al.

Page 1 of 1

It is certified that error appears in the above-identified patent and that said Letters Patent is hereby corrected as shown below:

Claim 21 should read:
The modular chemiresistive sensor system of claim 18 wherein the polymer nanowire are modified by amide coupling to covalently bind Aβ monomers or oligomers, said modular chemiresistive sensor system suitable for quantitatively detecting Alzheimer-associated biomarkers.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*